United States Patent [19]

Kalvelage

[11] 4,040,186

[45] Aug. 9, 1977

[54] ORTHODONTIC PLIER-TYPE TOOL

[76] Inventor: Gerald J. Kalvelage, 7035 Rosemary, Dearborn Heights, Mich. 48128

[21] Appl. No.: 402,394

[22] Filed: Oct. 1, 1973

[51] Int. Cl.² ............................................. A61C 7/00
[52] U.S. Cl. .................................................... 32/66
[58] Field of Search ........................... 32/66, 14, 40 R

[56] References Cited

U.S. PATENT DOCUMENTS

| 1,670,361 | 5/1928 | Johnson | 32/40 R |
|---|---|---|---|
| 3,581,400 | 6/1971 | Sneed | 32/66 |
| 3,727,316 | 4/1973 | Goldberg | 32/66 |

OTHER PUBLICATIONS

Dentronix, Catalogue No. 3, p. 2, Copyright 1972, Box 65, 925 Penna. Blvd., Feasterville, Pa. 19047.

Arista Dental Catalogue, p. 2, Surgical Company, 67 Lexington Ave., N.Y., N.Y.

Primary Examiner—Robert Peshock
Attorney, Agent, or Firm—Robert G. Mentag

[57] ABSTRACT

A plier-type tool for orthodontists for manipulating elastic ligatures and including a pair of pivoted plier members with each having a handle portion and a jaw portion. The outer end portion of each of said jaw portions comprises a pointed beak member which is disposed at an acute angle from a plane passing through the longitudinal axes of the handle portions. Each of said beak members is provided on the inner face thereof, near the pointed end thereof, with a concave groove, whereby an elastic ligature may be positioned in the grooves of said beak members and grasped between the beak members when they are moved to a closed position for manipulation of said elastic ligature.

1 Claim, 4 Drawing Figures

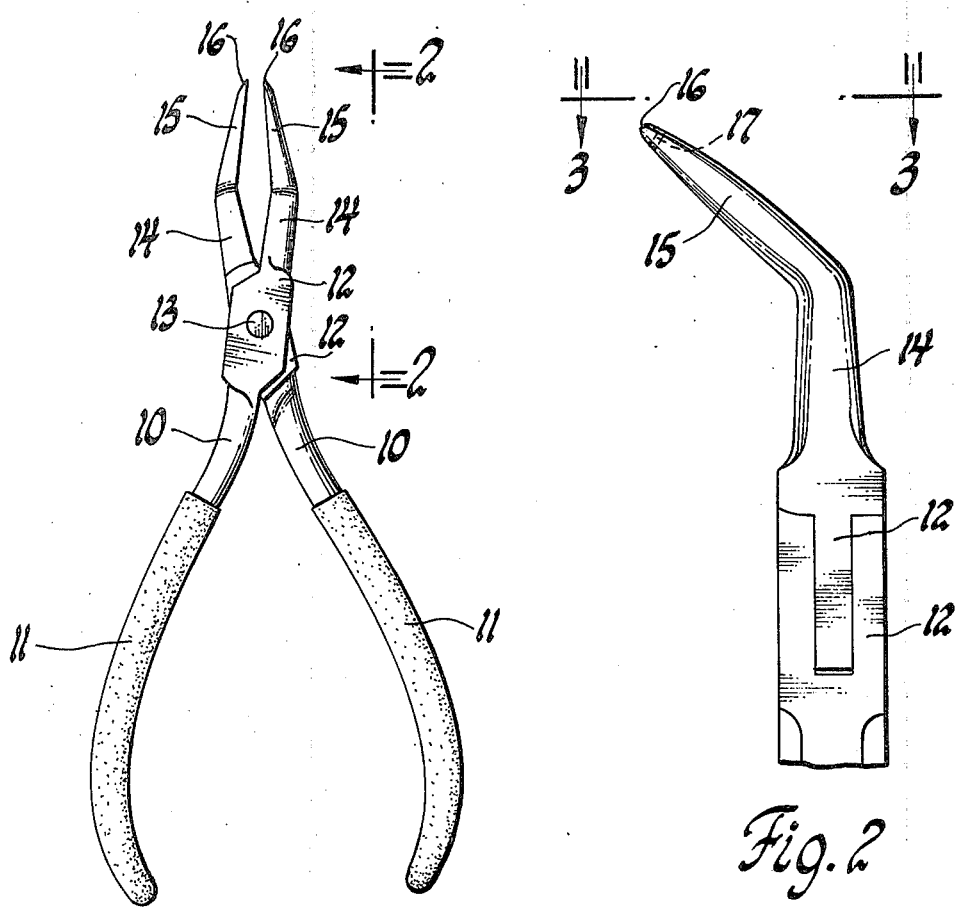
Fig.1
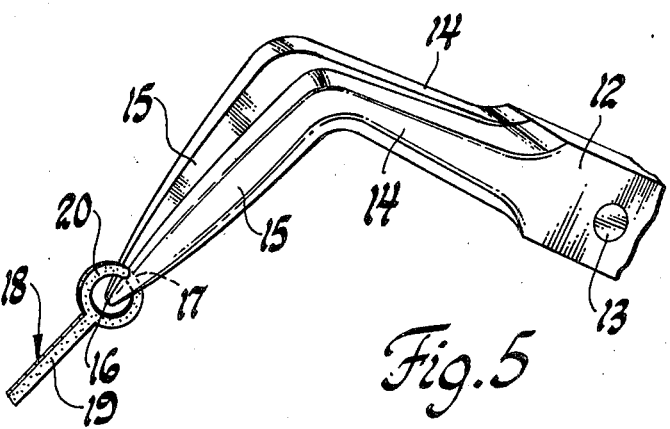
Fig.2
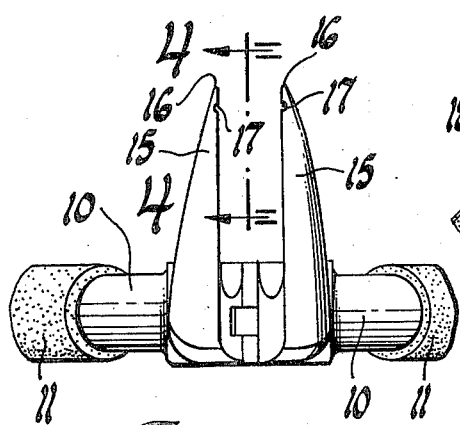
Fig.3
Fig.5
Fig.4

ORTHODONTIC PLIER-TYPE TOOL

BACKGROUND OF THE INVENTION

1. Field of the Invention

This invention relates generally to the dental art, and more particularly, to a plier-type tool adapted for use in the field of orthodontic dentistry.

2. Description of the Prior Art

One of the functions of orthodontics is the correcting of the irregular arrangement of teeth in the dental arch. The conventional technique for correcting such irregular arrangements of teeth includes the use of mounting a metal band with a bracket on each tooth. Corrective forces are then imparted to selected teeth by means of wires, springs and tensioning devices, including elastic ligatures in the form of elastic O-rings and the like. In attaching such elastic ligatures to said brackets for imparting corrective forces, it is necessary to grasp the O-rings and manipulate them into various configurations; for example, a FIG. 8. Heretofore, in order to manipulate such elastic ligatures, an instrument known in the art as a Matthew needle holder has been used. A disadvantage of said needle holder is that it has a serrated edge which tends to tear such elastic ligatures during manipulation of the same. A further disadvantage of said needle holder is that it is difficult to manipulate an elastic ligature with said needle holder when working in the molar area of the mouth of a patient. Also, in many instances it is necessary to stretch an O-ring type elastic ligature for attaching the same to a band bracket, and said needle holder is not capable of carrying out such function.

The present invention provides a plier-type tool which overcomes the aforementioned disadvantages of the prior art elastic ligature applying devices. The orthodontic plier-type tool of the present invention permits the user to quickly and firmly grasp an elastic ligature, such as an O-ring type ligature, and quickly and easily position the elastic ligature in an operative position on said band brackets. The plier-type tool of the present invention permits the user to stand at the back of a patient and permit the rolling of the wrist of the user to assist in the mounting and positioning of an elastic ligature. The plier-type tool of the present invention also permits the quick and easy stretching of an elastic O-ring ligature, followed by a grasping and inserting of the same into an operative position.

SUMMARY OF THE INVENTION

This invention relates to a plier-type tool adapted for use in the field of orthodontic dentistry and in particular a plier-type tool especially adapted for manipulating elastic ligatures.

It is an important object of the present invention to provide a novel and improved plier-type tool for orthodontists for manipulating elastic ligatures and which is simple and compact in construction, economical to manufacture and efficient in use.

It is another object of the present invention to provide a novel and improved plier-type tool for orthodontists which includes a pair of pointed beak members which are each provided with a groove on the inner face thereof for grasping an elastic ligature between the beak members for manipulating the same without tearing or damaging the ligature.

It is still another object of the present invention to provide a novel and improved plier-type tool for orthodontists which is provided with a pair of angled and pointed beak members which permits an orthodontist to stand in back of a patient and work in the molar area, at right angles thereto, in an efficient and expeditious manner. The angled beak members are each provided with a slot on the inner face thereof, near the pointed end of the beak members, for grasping an elastic ligature and hooking it onto an orthodontic bracket mounted on a patient's tooth. The angled beak members permit the user of the tool to roll his wrist in manipulating an elastic ligature grasped by the tool during an application of the ligature.

It is a further object of the present invention to provide a novel and improved plier-type tool for orthodontists which is provided with a pair of angled, pointed beak members for insertion through an O-ring type elastic ligature stretching the ligature, and then grasping the ligature and applying the same on an orthodontic bracket mounted on the tooth of a patient.

Other objects, features and advantages of this invention will be apparent from the following detailed description, appended claims, and the accompanying drawing.

BRIEF DESCRIPTION OF THE DRAWING

FIG. 1 is a plan view of an orthoodontic plier-type tool made in accordance with the principles of the present invention.

FIG. 2 is a fragmentary, enlarged elevational right side view of the structure shown in FIG. 1, taken along the line 2—2 thereof, and looking in the direction of the arrows.

FIG. 3 is a top end view of the structure illustrated in FIG. 2, taken along the line 3—3 thereof, and looking in the direction of the arrows.

FIG. 4 is a fragmentary, elevational view of the structure illustrated in FIG. 3, taken along the line 4—4 thereof, and looking in the direction of the arrows.

FIG. 5 is a fragmentary, perspective view of an orthodontic plier-type tool made in accordance with the principles of the present invention, and showing the tool grasping an O-ring on an elastic ligature.

DESCRIPTION OF THE PREFERRED EMBODIMENT

Referring now to the drawing, FIG. 1 shows a plier-type tool for orthodontists for manipulating elastic ligatures and which includes a pair of pivotally mounted plier members. Each of the plier members includes a curved handle portion 10 which is provided with a plastic grip protector indicated by the numeral 11. Each of the plier members also includes a jaw portion, integrally formed on the upper end of each of the handle portions, and which includes a pivot portion 12, an intermediate portion 14, and an outer end portion or beak member 15. As viewed in FIG. 1, the left handle portion may be termed the left-hand member and the right handle portion may be termed by the right-hand member. Each of the jaw pivot portions 12 is pivotally connected by any suitable means, as by a suitable pivot portion 13.

As best seen in FIG. 2, each of the intermediate jaw portions 14 in integrally connected to its respective jaw pivot portion 12. Integrally formed on the outer end of each of the jaw intermediate portions 14 is a pointed and angled outer end portion or beak member 15.

Each of the beak members 15 is disposed at an acute angle from a plane member passing through the longitudinal axes of the handle portions 10, to permit the user to reach back into the posterior of the mouth so as to work at right angles to teeth in the molar area. The beak members 15 may be disposed at an acute angle in a range up to and including 90° from said plane.

As illustrated in FIGS. 3 and 4, the beak members 15 are provided with a pointed outer end 16, and the inner opposed faces of the beak members 15 are parallel to each other. A groove 17, which is concave in transverse configuration, is formed in the inner face of each of the beak members 15 adjacent the pointed end 16. Each of the grooves 17 is disposed perpendicular to the longitudinal axis of its respective beak member 15.

As shown in FIG. 5, the plier-type tool of the present invention is adapted for manipulating elastic ligatures of the type illustrated generally by the numeral 18. The elastic ligature 18 is of the type which includes an elongated elastic arm 19 that has integrally formed on each end thereof an O-ring 20. The concave groove 17 permits the user of the tool of the present invention to grasp a ligature O-ring 20, as shown in FIG. 5, for manipulating the same for placing it in an operative position on brackets on an orthodontic band on a tooth in the mouth of a patient. The grooves 17 may be made to any desired size, for example, to a radius of approximately one-half to one millimeter. The thickness of the O-rings of the elastic ligatures varies from one to two millimeters.

In use, the plier-type tool of the present invention would be manipulated to an open position and an O-ring as 20 seated in the groove of one of the beak members 15, and the other beak member 15 would then be closed thereover so as to grasp the O-ring 20 in the circular groove formed by the half-round grooves 17 in each of the beak members 15. The elastic ligature may be quickly and easily mounted in place on an orthodontic bracket in the mouth of a patient in a quick and easy manner and without tearing or damaging the elastic ligature. In some instances, the elastic ligatures are made from a stiff material, whereby it is necessary to first spread the O-rings on the elastic ligature before mounting the same in place. In the last-mentioned situation, the pointed beak members 15 would be brought together and inserted into an O-ring and the O-ring moved up the pointed beak member 15 to spread the O-ring. The stretched or spread O-ring is then moved off the beak member and quickly grasped and mounted in an operative position before it has a chance to return its original condition. The plier-type tool of the present invention provides a safe and efficeint tool for stretching an elastic ligature, because the construction of the tool permits it to be moved in a direction away from the patient as the elastic ligature is stretched, so that if the elastic ligature does break, the movement of the tool being in a direction away from the patient, the patient cannot be accidentally gouged with the tool in any manner. Experience has shown that the plier-type tool of the present invention is a practical and efficient tool for use in the art of orthodontic dentistry.

While it will be apparent that the preferred embodiment of the invention herein disclosed is well calculated to fullfill the objects above stated, it will be appreciated that the invention is susceptible to modification, variation and change.

What is claimed is:

1. A plier-type tool for orthodontists for manipulating O-ring type elastic ligatures comprising:
  a. a pair of plier members, each having a handle portion and a jaw portion;
  b. said plier members being retained in a pivotal relationship by a pivot pin;
  c. said plier members being movable between an open position and a closed position by manipulation of the handle portions of the plier members;
  d. each of said jaw portions including a pivot portion, an intermediate portion and an outer end portion;
  e. each of said outer end portions comprising a beak member having an inner face, with each of said beak members having a transverse groove formed along the inner face thereof, whereby an elastic ligature may be positioned lengthwise in said grooves and grasped between said beak members for manipulating said elastic ligature when the jaw portions are moved to the closed position;
  f. each of said beak members having an identical pointed outer end configuration adjacent the transverse groove formed thereon and forming one-half of a total pointed tip formed by the beak members when in the closed position, whichwhen in the closed position facilitates the sliding thereon of an elastic ligature for expanding the same preparatory to grasping the ligature by the beak members for manipulation and placement of the same in an operative position in a patient's mouth;
  g. each of said grooves in said beak members having a concave transverse configuration that extends perpendicular to the longitudinal axis of each beak member and which coact together to form a transversely closed circular groove when the jaw portions are moved to the closed position to completely surround said ligature;
  h. each of said beak members being disposed at an acute angle from a plane passing through the longitudinal axes of the handle portions; and,
  i. said acute angle being an acute angle in a range up to and including 90°.

* * * * *

UNITED STATES PATENT OFFICE
CERTIFICATE OF CORRECTION

Patent No. 4,040,186                Dated August 9, 1977

Inventor(s) Gerald J. Kalvelage

It is certified that error appears in the above-identified patent and that said Letters Patent are hereby corrected as shown below:

Column 1, line 13, "arrangements" should be ---arrangement---.
Column 1, line 21, 8, following "Fig." should be ---"8"---.
Column 2, line 17, following "ligature", first occurrence, insert ---for initially---.
Column 2, line 58, following "termed", delete the word ---by---.
Column 2, line 63, following "portions 14", "in" should be ---is---.
Column 3, line 25, following "size", insert the word ---as---.

Signed and Sealed this

*Twenty-fifth* Day of *October 1977*

[SEAL]

Attest:

RUTH C. MASON          LUTRELLE F. PARKER
*Attesting Officer*      *Acting Commissioner of Patents and Trademarks*